United States Patent
Ignatyev et al.

(10) Patent No.: US 8,927,714 B2
(45) Date of Patent: Jan. 6, 2015

(54) PROCESS FOR PREPARING DIHYDRIDODICYANOBORATE SALTS

(75) Inventors: Nikolai (Mykola) Ignatyev, Duisburg (DE); Michael Schulte, Bischofsheim (DE); Eduard Bernhardt, Wuppertal (DE); Vera Bernhardt-Pitchougina, Wuppertal (DE); Helge Willner, Muehlheim/Ruhr (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/119,559

(22) PCT Filed: May 23, 2012

(86) PCT No.: PCT/EP2012/002178
§ 371 (c)(1),
(2), (4) Date: Nov. 22, 2013

(87) PCT Pub. No.: WO2012/163488
PCT Pub. Date: Dec. 6, 2012

(65) Prior Publication Data
US 2014/0114074 A1    Apr. 24, 2014

(30) Foreign Application Priority Data

May 31, 2011   (DE) .......................... 10 2011 103 754

(51) Int. Cl.
*C07F 5/02*  (2006.01)
*C01B 6/21*  (2006.01)

(52) U.S. Cl.
USPC ............................................. 546/13; 556/8

(58) Field of Classification Search
USPC ................................................ 546/13; 556/8
See application file for complete search history.

(56) References Cited

U.S. PATENT DOCUMENTS 3,697,232 A   10/1972 Wade

FOREIGN PATENT DOCUMENTS

DE    2028569 A1    2/1971
GB    1295139 A    11/1972
WO    2008102661 A1    8/2008

OTHER PUBLICATIONS

Gyori, B. et al., "Preparation and properties of novel cyano and isocyano derivatives of borane and the tetrahydroborate anion," Journal of Organometallic Chemistry, 1983, vol. 255, pp. 17-18.
International Search Report for PCT/EP2012/002178 dated Jul. 23, 2012.
Spielvogel, B. F. et al., "Synthesis of sodium and tetra-n-butylammonium Dicyanodihydroborates," Inorg. Chem., 1984, vol. 23, pp. 3263-3265.
Egan, P. G. et al., "[(Ph2MeP)3Cu(NC)2BH2] and P3Cu(NC)2BH2 (P3=1,1,1-Tris((diphenylphosphino)methyl)ethane): The First Metal Complexes of Dicyanodihydroborate," Inorg. Chem., 1984, vol. 23, pp. 2203-2204.
Das, M. et al., "Studies on the Reactivity of Dicyanodihydroborate with some Lewis base Hydrochlorides," The Chemical Society of Japan, Apr. 1990, vol. 63, pp. 1281-1283.
Zhang, Y. et al "Dicyanoborate-based ionic liquids as hypergolic fluids," Angew. Chem., 2011, vol. 123, pp. 965-967.
Evers, E. C. et al., "Interaction of diborane with silyl cyanides," Contribution for the John Harrison Laboratory of Chemistry, University of Pennsylvania, and the Department of Chemistry, Illinois Institute of Technology, Sep. 5, 1959, vol. 81, pp. 4493-4496.
Wade, R. C. et al., "Synthesis of Sodium Cyanotrihydroborate and Sodium Isocyanotrihydroborate," Inorganic Chemistry, 1970, vol. 9, No. 9, pp. 2146-2150.
Hutchins, R. O. et al., "Tetrabutylammonium Cyanoborohydride. A New, exceptionally selective reducing reagent," J. Am. Chem. Soc., 1973, vol. 95, No. 18, pp. 6131-6133.
Emri, J. et al., "A new method for the synthesis of cyanohydroborates and cyanoborane complexes," J. Chem. Soc., Chem. Comm., 1983, pp. 1303-1304.
Wittig, V. G. et al., "Uber Komplexbildung mit Triphenyl-bor (III. Mitt.1)," Liebigs Ann. Chem., 1951, vol. 573, pp. 195-209.
Toyo Kasei Kogyo Co Ltd., "Method for producing trialkylsilylnitrile," Espacenet, Publication Date: Aug. 28, 2008; English Abstract of WO-2008102661.

*Primary Examiner* — Charanjit Aulakh
(74) *Attorney, Agent, or Firm* — Millen, White, Zelano & Branigan, P.C.

(57) ABSTRACT

The invention relates to a process for the preparation of alkali-metal salts with dihydridodicyanoborate anions by reaction of alkali-metal tetrahydridoborates or trihydridocyanoborates with trialkylsilyl cyanide and further reaction thereof in metathesis reactions.

7 Claims, No Drawings

PROCESS FOR PREPARING DIHYDRIDODICYANOBORATE SALTS

The invention relates to a process for the preparation of alkali-metal salts with dihydridodicyanoborate anions by reaction of alkali-metal tetrahydridoborates or trihydridocyanoborates with trialkylsilyl cyanide and further reaction thereof in metathesis reactions.

A synthesis of lithium $[BH_2(CN)_2]$ is known, for example, from B. Györi et al, Journal of Organometallic Chemistry, 1983, 255, 17-28, where oligomeric $1/n\ (BH_2CN)_n$ is reacted with $LiCN*CH_3CN$ in dimethyl sulfide.

A synthesis of sodium $[BH_2(CN)_2]$ is known, for example, from B. F. Spielvogel et al, Inorg. Chem. 1984, 23, 3262-3265, where a complex of anilline with $BH_2CN$ is reacted with sodium cyanide. Tetrahydrofuran is described as solvent. P. G. Egan et al, Inorg. Chem. 1984, 23, 2203-2204, also describe the synthesis of the dioxane complex $Na[BH_2(CN)_2]*0.65$ (dioxane) based on the papers by Spielvogel et al., using a different work-up variant.

M. K. Das et al, Bull. Chem. Soc. Jpn., 1990, 63, 1281-1283, report on reactions of the dioxane complex $Na[BH_2(CN)_2]*0.65$ (dioxane), prepared by the method of P. G. Egan et al, with amine hydrochlorides or phosphine hydrochlorides. In general, the metathesis product is formed here, i.e. quaternary ammonium or phosphonium dicyanodihydridoborates, such as, for example, propylammonium dicyanodihydridoborate, bis(isopropyl)ammonium dicyanodihydridoborate, tripropylammonium dicyanodihydridoborate, s-butylammonium dicyanodihydridoborate, dibutylammonium dicyanodihydridoborate, bis(isobutyl)ammonium dicyanodihydridoborate, triphenylphosphonium dicyanodihydridoborate, diethylammonium dicyanodihydridoborate or triethylammonium dicyanodihydridoborate.

Compounds with organic cations and dicyanodihydridoborate anion are known, for example, from Zhang Y. and Shreeve J. M., Angew. Chem. 2011, 123, 965-967, where the compounds were prepared by anion exchange with $Ag[BH_2(CN)_2]$. A synthesis of this silver dicyanodihydridoborate is not described.

However, there continues to be a demand for economical alternative synthesis methods for the preparation of this interesting class of salts with dicyanodihydridoborate anion, in particular of alkali-metal, ammonium or tetraalkylammonium salts.

The object of the present invention is therefore to develop an alternative preparation process which gives the desired salts in good yield and starts from readily accessible starting materials.

Surprisingly, it has been found that alkali-metal tetrahydridoborates or cyanotrihydridoborates are excellent starting materials for the synthesis of the desired dicyanodihydridoborates, which are readily accessible or commercially available.

The invention therefore relates to a process for the preparation of salts of the formula I $$Me^+[BH_2(CN)_2]^-\qquad\qquad I,$$

where $Me^+$ is a lithium, potassium, sodium, caesium or rubidium cation, by reaction of a salt of the formula II or of the formula III $$Me^+[BH_4]^-\qquad\qquad II,$$

$$Me^+[BH_3(CN)]^-\qquad\qquad III,$$

where
$Me^+$ has an above-mentioned meaning, with a trialkylsilyl cyanide, where the alkyl group of the trialkylsilyl cyanide in each case, independently of one another, denotes a linear or branched alkyl group having 1 to 4 C atoms.

The process according to the invention is surprising, since a similar reaction of the diborane $B_2H_6$ with trialkylsilyl cyanide merely gives a complex $(CH_3)_3SiCN*BH_3$, which decomposes thermally into gaseous $(CH_3)_3SiH$ and solid $BH_2CN$ in polymeric form. (E. C. Evers et al., J. of American Chemical Society, 81, 1959, 4493-4496).

The process according to the invention can also be used for the synthesis of ammonium or tetraalkylammonium dicyanodiydridoborates, where the alkyl group of the tetraalkylammonium cation in each case, independently of one another, denotes a linear or branched alkyl group having 1 to 12 C atoms. Preferred tetraalkylammonium cations are the tetramethylammonium, tetraethylammonium or tetrabutylammonium cation.

A straight-chain or synonymously linear or branched alkyl group having 1 to 4 C atoms is, for example, methyl, ethyl, n-propyl, isopropyl, n-butyl, sec-butyl or tert-butyl. A linear or branched alkyl group having 1 to 12 C atoms encompasses the embodiments of the linear or branched alkyl group having 1 to 4 C atoms and, for example, n-pentyl, n-hexyl, n-heptyl, n-octyl, ethylhexyl, n-nonyl, n-decyl, n-undecyl or n-dodecyl.

The alkyl groups of the trialkylsilyl cyanide may be identical or different. The alkyl groups are preferably identical. Examples of trialkylsilyl cyanides are therefore trimethylsilyl cyanide, triethylsilyl cyanide, triisopropylsilyl cyanide, tripropylsilyl cyanide or tributylsilyl cyanide. Particular preference is given to the use of trimethylsilyl cyanide, which is commercially available or can also be prepared in situ.

The compounds of the formula II or III are commercially available or accessible by known synthesis processes. The cyanotrihydridoborates of the formula III are prepared, for example, in accordance with Wittig et al., Liebigs Ann. Chem. 1951, 573, 195, by reaction, for example, of lithium borohydride with prussic acid with formation of hydrogen in diethyl ether. R. C. Wade et al., Inorganic Chemistry, 9 (9), 1970, 2146-2150, describe the synthesis of sodium trihydridocyanoborate by reaction of sodium borohydride with prussic acid in THF. DE 2028569 A (1971) and U.S. Pat. No. 3,697,232 A (1972) describe the synthesis of compounds of the formula (III), as described above, in solvated form by reaction of a metal tetrahydroborate, $Me[BH_4]$, with HCN in anhydrous organic solvents.

R. O. Hutchins et al., J. of American Chemical Society, 95 (18), 1973, 6131-6133, describes the synthesis of tetrabutylammonium trihidridocyanoborate by anion exchange, where tetrabutylammonium hydrogensulfate is reacted with sodium trihydridocyanoborate. Tetrabutylammonium trihydridocyanoborate is a solid having a melting point of 144-145° C.

Preference is given to the use of compounds of the formula II or III in which $Me^+$ is a lithium, sodium or potassium cation, particularly preferably a sodium or potassium cation, very particularly preferably a sodium cation.

Very particularly preferred compounds of the formula II or III for the synthesis of the compounds of the formula I, as described above, should therefore be selected from sodium tetrahydridoborate (or synonymously sodium borohydride) or sodium trihydridocyanoborate.

Compounds of the formula II, as described above, or preferred compounds of the formula II are especially preferably employed in the process according to the invention.

The preparation according to the invention of the compounds of the formula I, as described above, is preferably carried out at temperatures between 10° and 200° C., in particular between 15° and 150° C., particularly preferably at 100° to 150° C.

The reaction of the compounds of the formula II or of the formula III, as described above, with the trialkylsilyl cyanide can be carried out without protective-gas atmosphere. However, the reaction is preferably carried out under dried air or in an inert-gas atmosphere.

The reaction of the compounds of the formula II or of the formula III, as described above, with the trialkylsilyl cyanide is preferably carried out without solvent. However, the reaction in the presence of an organic solvent, for example in the presence of nitriles or ethers, is possible. A preferred nitrile is acetonitrile. Preferred ethers are tetrahydrofuran, diethyl ether or di methoxyethane.

In a further embodiment, the trialkylsilyl cyanide used is prepared in situ from an alkali-metal cyanide and a trialkylsilyl chloride in the presence of an alkali-metal iodide or fluoride and optionally iodine, before the reaction with a compound of the formula II or III, as described above. Sodium cyanide and sodium iodide or potassium cyanide and potassium iodide is preferably used here, where the alkali-metal iodide is preferably added in a molar amount of 0.1 mol/l, based on 1 mol/l of alkali-metal cyanide and trialkylsilyl chloride. In general, this preparation process is based on the description by M. T. Reetz, I. Chatziiosifidis, Synthesis, 1982, p. 330; J. K. Rasmussen, S. M. Heilmann and L. R. Krepski, The Chemistry of Cyanotrimethylsilane in G. L. Larson (Ed.) "Advances in Silicon Chemistry", Vol. 1, p. 65-187, JAI Press Inc., 1991 or WO 2008/102661 A1.

The invention therefore also relates to a process for the preparation of compounds of the formula I, as described above, characterised in that the trialkylsilyl cyanide is prepared in situ from an alkali-metal cyanide and a trialkylsilyl chloride in the presence of an alkali-metal iodide and optionally iodine before the reaction with a compound of the formula II or formula III.

When carrying out the preparation according to the invention of compounds of the formula I, as described above, it is possible to purify the compounds obtained from the reaction and to employ them as isolated, pure compound in a salt-exchange reaction or metathesis reaction, preferably with compounds of the formula IV, as described below.

However, it is advantageous, in a further embodiment, for the compound of the formula I not to be worked up to give the pure substance, but instead merely the byproducts which are insoluble in organic solvents or are volatile, such as, for example, trialkylsilane or an excess of trimethylsilyl cyanide, to be separated off and the compound of the formula I to be reacted, without further purification to give the pure substance, with a compound of the formula IV, as described below.

The invention likewise furthermore relates to a process as described above in detail, in which, in a subsequent reaction, a compound of the formula I is reacted with a compound of the formula IV $$KtA \qquad\qquad IV$$

in which
Kt has the meaning of an organic cation or a metal cation, where the cation Kt does not correspond to the cation $Me^+$ employed in the compound of the formula I and
the anion A denotes
$F^-$, $Cl^-$, $Br^-$, $I^-$, $OH^-$, $[HF_2]^-$, $[CN]^-$, $[SCN]^-$, $[R_1COO]^-$, $[R_1OC(O)O]^-$, $[R_1SO_3]^-$, $[R_2COO]^-$, $[R_2SO_3]^-$, $[R_1OSO_3]^-$, $[PF_6]^-$, $[BF_4]^-$, $[HSO_4]^{1-}$, $[NO_3]^-$, $[(R_2)_2P(O)O]^-$, $[R_2P(O)O_2]^{2-}$, $[(R_1O)_2P(O)O]^-$, $[(H_1O)P(O)O_2]^{2-}$, $[(R_1O)R_1P(O)O]^-$, tosylate, malonate, which may be substituted by straight-chain or branched alkyl groups having 1 to 4 C atoms, $[HOCO_2]^-$ or $[CO_3]^{2-}$, where $R_1$ in each case, independently of one another, denotes a straight-chain or branched alkyl group having 1 to 12 C atoms and
$R_2$ in each case, independently of one another, denotes a straight-chain or branched perfluorinated alkyl group having 1 to 12 C atoms and where electroneutrality is taken into account in the formula of the salt KtA.

A perfluorinated linear or branched alkyl group having 1 to 4 C atoms is, for example, trifluoromethyl, pentafluoroethyl, n-heptafluoropropyl, iso-heptafluoropropyl, n-nonafluorobutyl, sec-nonafluorobutyl or tert-nonafluorobutyl. $R_2$ defines analogously a linear or branched perfluorinated alkyl group having 1 to 12 C atoms, encompassing the above-mentioned perfluoroalkyl groups and, for example, perfluorinated n-hexyl, perfluorinated n-heptyl, perfluorinated n-octyl, perfluorinated ethylhexyl, perfluorinated n-nonyl, perfluorinated n-decyl, perfluorinated n-undecyl or perfluorinated n-dodecyl.

$R_2$ is particularly preferably trifluoromethyl, pentafluoroethyl or nonafluorobutyl, very particularly preferably trifluoromethyl or pentafluoroethyl.

$R_1$ is particularly preferably methyl, ethyl, n-butyl, n-hexyl or n-octyl, very particularly preferably methyl or ethyl.

Substituted malonates are, for example, the compounds—methyl or ethyl malonate.

The anion A of the formula IV is preferably $OH^-$, $Cl^-$, $Br^-$, $I^-$, $[CH_3SO_3]^-$ $[CH_3OSO_3]^-$, $[CF_3COO]^-$, $[CF_3SO_3]^-$, $[(C_2F_5)_2P(O)O]^-$ or $[CO_3]^{2-}$, particularly preferably $OH^-$, $Cl^-$, $Br^-$, $[CH_3OSO_3]^-$, $[CF_3SO_3]^-$, $[CH_3SO_3]^-$ or $[(C_2F_5)_2P(O)O]^-$.

The organic cation for Kt is selected, for example, from ammonium cations, sulfonium cations, oxonium cations, phosphonium cations, uronium cations, thiouronium cations, guanidinium cations or heterocyclic cations, as described below, in particular by the formulae (1) to (8), or tritylium.

Kt is particularly preferably an
oxonium cation of the formula $$[(R^o)_3O]^+ \qquad\qquad (1)$$

or a sulfonium cation of the formula $$[(R^o)_3S]^+ \qquad\qquad (2),$$

where $R^o$ in each case, independently of one another, denotes a straight-chain or branched alkyl group having 1-8 C atoms, unsubstituted phenyl, phenyl which is substituted by $R^{1*}$, OR', $N(R')_2$, CN or halogen or, restricted to sulfonium cations of the formula (2), $(R''')_2N$—,
where R' in each case, independently of one another, denotes H, unfluorinated, partially fluorinated or perfluorinated linear or branched $C_1$- to $C_{18}$-alkyl, saturated $C_3$- to $C_7$-cycloalkyl, unsubstituted or substituted phenyl, $R^{1*}$ in each case, independently of one another, denotes unfluorinated, partially fluorinated or perfluorinated linear or branched $C_1$- to $C_{18}$-alkyl, saturated $C_3$- to $C_7$-cycloalkyl, unsubstituted or substituted phenyl and R''' in each case, independently of one another, denotes linear or branched alkyl having 1 to 6 C atoms,
or an ammonium cation of the formula (3), $$[NR_4]^+ \qquad\qquad (3),$$

where
R in each case, independently of one another, denotes
H, OR', N(R')$_2$, with the proviso that a maximum of one substituent R in formula (3) is OR' or N(R')$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two substituents R may be fully substituted by halogens, in particular —F and/or —Cl or where one or more substituents R may be partially substituted by halogens, in particular —F and/or —Cl, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R',
and where one or two carbon atoms of the R which are not adjacent and are not in the α-position may be replaced by atoms and/or atom groups selected from the group —O—, —S—, —S(O)—, —SO$_2$—, —SO$_2$O—, —C(O)—, —C(O)O—, —N$^+$(R'$_2$)—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' in each case, independently of one another, denotes H, unfluorinated, partially fluorinated or perfluorinated, linear or branched $C_1$- to $C_{18}$-alkyl, saturated $C_3$- to $C_7$-cycloalkyl, unsubstituted or substituted phenyl and X in each case, independently of one another, denotes halogen.
or a phosphonium cation of the formula (4),

$$[P(R^2)_4]^+ \qquad (4),$$

where
R$^2$ in each case, independently of one another, denotes
H, OR' or N(R')$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two substituents R$^2$ may be fully substituted by halogens, in particular —F and/or —Cl or where one or more substituents R$^2$ may be partially substituted by halogens, in particular —F and/or —Cl, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R',
and where one or two carbon atoms of the R$^2$ which are not adjacent and are not in the α-position may be replaced by atoms and/or atom groups selected from the group —O—, —S—, —S(O)—, —SO$_2$—, —SO$_2$O—, —C(O)—, —C(O)O—, —N$^+$(R'$_2$)—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' in each case, independently of one another, denotes H, unfluorinated, partially fluorinated or perfluorinated, linear or branched $C_1$- to $C_{18}$-alkyl, saturated $C_3$- to $C_7$-cycloalkyl, unsubstituted or substituted phenyl and X in each case, independently of one another, denotes halogen,
or a uronium cation of the formula (5), $$[C(NR^3R^4)(OR^5)(NR^6R^7)]^+ \qquad (5),$$

or that Kt is a thiouronium cation of the formula (6),

$$[C(NR^3R^4)(SR^5)(NR^6R^7)]^+ \qquad (6),$$

where
R$^3$ to R$^7$ each, independently of one another, denote
H, where H is excluded for R$^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two of the substituents R$^3$ to R$^7$ may be fully substituted by halogens, in particular —F and/or —Cl, and one or more of the substituents R$^3$ to R$^7$ may be partially substituted by halogens, in particular —F and/or —Cl, and/or —OH, —OR', —N(R')$_2$, —CN, —C(O)OH, —C(O)OR', —C(O)R', —C(O)N(R')$_2$, —SO$_2$NR'$_2$, —C(O)X, —SO$_2$OH, —SO$_2$X, —SR', —S(O)R', —SO$_2$R', —NO$_2$ and where one or two carbon atoms of R$^3$ to R$^7$ which are not adjacent and are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' in each case, independently of one another, denotes H, unfluorinated, partially fluorinated or perfluorinated, linear or branched $C_1$- to $C_{18}$-alkyl, saturated $C_3$- to $C_7$-cycloalkyl, unsubstituted or substituted phenyl and X in each case, independently of one another, denotes halogen,
or a guanidinium cation of the formula (7), $$[C(NR^8R^9)(NR^{10}R^{11})(NR^{12}R^{13})]^+ \qquad (7),$$

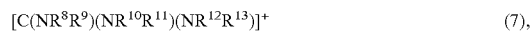

where
R$^8$ to R$^{13}$ each, independently of one another, denote
H, —CN, N(R')$_2$, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two of the substituents R$^8$ to R$^{13}$ may be fully substituted by halogens, in particular —F and/or —Cl, and one or more of the substituents R$^8$ to R$^{13}$ may be partially substituted by halogens, in particular —F and/or —Cl, and/or —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$ and where one or two carbon atoms of R$^8$ to R$^{13}$ which are not adjacent and are not in the α-position may be replaced by atoms and/or atom groups selected from the group —O—, —S—, —S(O)—, —SO$_2$—, —SO$_2$O—, —C(O)—, —C(O)O—, —N$^+$(R'$_2$)—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' in each case, independently of one another, denotes H, unfluorinated, partially fluorinated or perfluorinated, linear or branched $C_1$- to $C_{18}$-alkyl, saturated $C_3$- to $C_7$-cycloalkyl, unsubstituted or substituted phenyl and X in each case, independently of one another, denotes halogen,
or a heterocyclic cation of the formula (8), $$[HetN]^{z+} \qquad (8),$$

where
HetN$^{z+}$ denotes a heterocyclic cation selected from the group

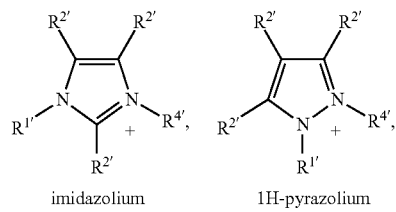
imidazolium     1H-pyrazolium

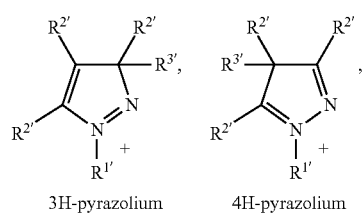
3H-pyrazolium     4H-pyrazolium

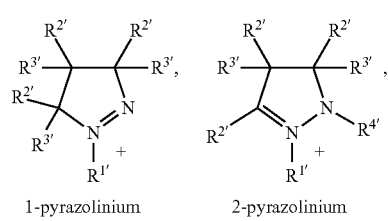
1-pyrazolinium     2-pyrazolinium

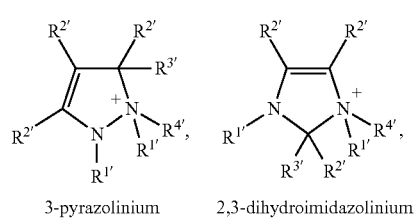
3-pyrazolinium     2,3-dihydroimidazolinium

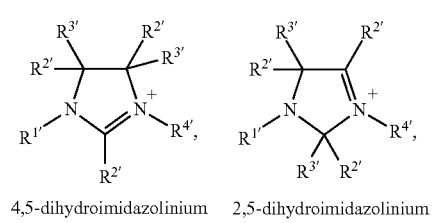
4,5-dihydroimidazolinium     2,5-dihydroimidazolinium

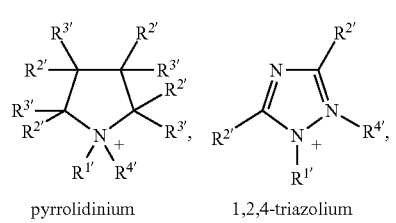
pyrrolidinium     1,2,4-triazolium

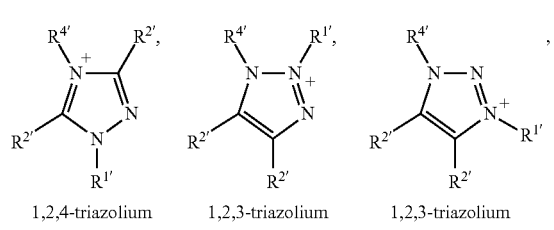
1,2,4-triazolium     1,2,3-triazolium     1,2,3-triazolium

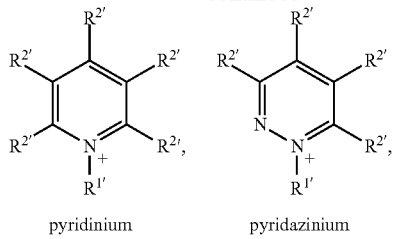
pyridinium     pyridazinium

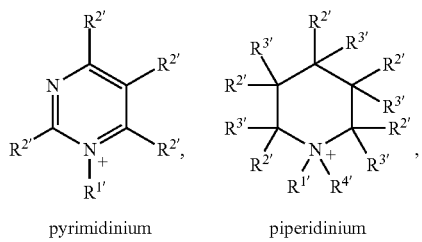
pyrimidinium     piperidinium

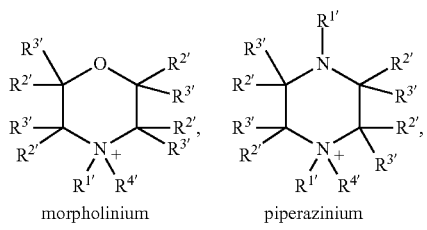
morpholinium     piperazinium

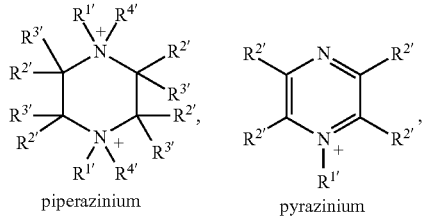
piperazinium     pyrazinium

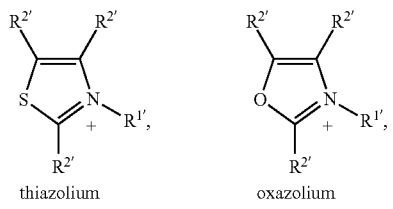
thiazolium     oxazolium

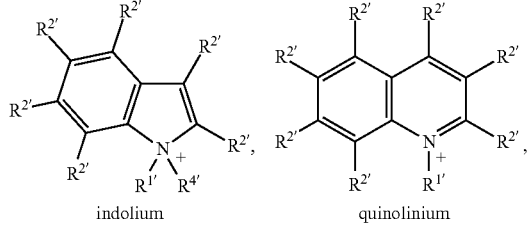
indolium     quinolinium

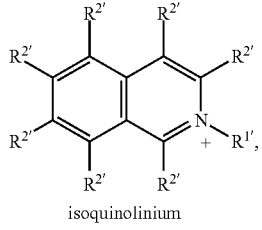
isoquinolinium

-continued quinoxalinium indolinium benzimidazolium where the substituents
$R^{1'}$ to $R^{4'}$ each, independently of one another, denote
H, with the proviso that $R^{1'}$ and $R^{4'}$ are not together H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
saturated, partially or fully unsaturated heteroaryl, heteroaryl-$C_1$-$C_6$-alkyl or aryl-$C_1$-$C_6$-alkyl and
$R^{2'}$ additionally denotes F, Cl, Br, I, —CN, —OR', —N(R')$_2$, —P(O)R'$_2$, —P(O)(OR')$_2$, —P(O)(N(R')$_2$)$_2$, —C(O)R', —C(O)OR', —C(O)X, —C(O)N(R')$_2$, —SO$_2$N(R')$_2$, —SO$_2$OH, —SO$_2$X, —SR', —S(O)R', —SO$_2$R' and/or NO$_2$, with the proviso that $R^{1'}$, $R^{3'}$ and $R^{4'}$ are then each, independently of one another, H and/or a straight-chain or branched alkyl having 1-20 C atoms and/or a straight-chain or branched alkenyl having 2-20 C atoms and one or more double bonds, where the substituents $R^{1'}$, $R^{2'}$, $R^{3'}$ and/or $R^{4'}$ together may also form a ring system,
where one, two or three substituents $R^{1'}$ to $R^{4'}$ may be fully substituted by halogens, in particular —F and/or —Cl, and one or more substituents $R^{1'}$ to $R^{4'}$ may be partially substituted by halogens, in particular —F and/or —Cl, and/or —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$, but where $R^{1'}$ and $R^{4'}$ cannot simultaneously be fully substituted by halogens,
and where one or two carbon atoms of the substituents $R^{1'}$ to $R^{4'}$ which are not adjacent and are not bonded to the heteroatom may be replaced by atoms and/or atom groups selected from —O—, —S—, —S(O)—, —SO$_2$—, —SO$_2$O—, —C(O)—, —C(O)O—, —N$^+$(R'$_2$)—, —P(O)R'O—, —C(O)NR'—, —SO$_2$NR'—, —OP(O)R'O—, —P(O)(N (R')$_2$)NR'—, —P(R')$_2$=N— or —P(O)R'—, where R' in each case, independently of one another, denotes H, unfluorinated, partially fluorinated or perfluorinated, linear or branched $C_1$- to $C_{18}$-alkyl, saturated $C_3$- to $C_7$-cycloalkyl, unsubstituted or substituted phenyl and X in each case, independently of one another, denotes halogen,
or a tritylium cation,
or a metal cation from groups 1 to 12 of the Periodic Table, selected from alkali-metal cations, Ag$^+$, Mg$^{2+}$, Cu$^+$, Cu$^{2+}$, Zn$^{2+}$, Ca$^{2+}$, Y$^{+3}$, Yb$^{+3}$, La$^{+3}$, Sc$^{+3}$, Ce$^{+3}$, Nd$^{+3}$, Tb$^{+3}$, Sm$^{+3}$ or complex (ligand-containing) metal cations which contain rare-earth, transition or noble metals, such as rhodium, ruthenium, iridium, palladium, platinum, osmium, cobalt, nickel, iron, chromium, molybdenum, tungsten, vanadium, titanium, zirconium, hafnium, thorium, uranium, gold.

Fully unsaturated cycloalkyl substituents in the sense of the present invention are also taken to mean aromatic substituents.

Suitable substituents R and $R^2$ to $R^{13}$ of the compounds of the formulae (1) to (7) in accordance with the invention are, besides H, preferably: straight-chain or branched $C_1$- to $C_{20}$—, in particular $C_1$- to $C_{14}$-alkyl groups, and saturated or unsaturated, i.e. also aromatic, $C_3$- to $C_7$-cycloalkyl groups, which may be substituted by straight-chain or branched $C_1$- to $C_6$-alkyl groups, in particular phenyl.

The substituents $R^0$, R and $R^2$ in the compounds of the formula (1), (2), (3) or (4) may be identical or different here. In compounds of the formulae (1), preferably two or three substituents $R^o$ are identical. In compounds of the formulae (2), preferably all substituents $R^o$ are identical or two are identical and one substituent is different. In compounds of the formula (3), preferably three or four substituents R are identical. In compounds of the formula (4), preferably three or four substituents $R^2$ are identical.

The substituents R and $R^2$ are particularly preferably methyl, ethyl, isopropyl, propyl, butyl, sec-butyl, pentyl, hexyl, octyl, decyl or tetradecyl.

Up to four substituents of the guanidinium cation $[C(NR^8R^9)(NR^{10}R^{11})—(NR^{12}R^{13})]^+$ may also be connected in pairs in such a way that mono-, bi- or polycyclic molecules form.

Without restricting generality, examples of guanidinium cations of this type are:

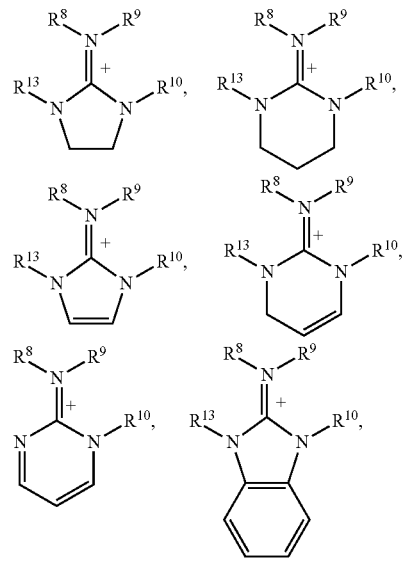

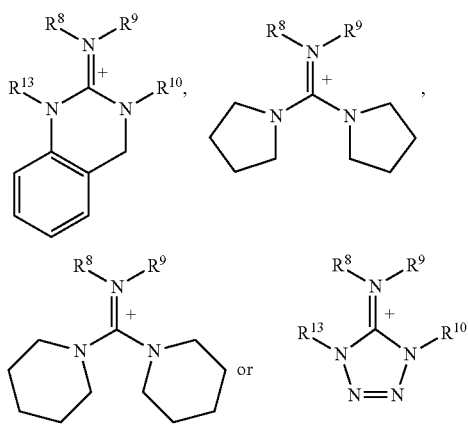

where the substituents $R^8$ to $R^{10}$ and $R^{13}$ can have an abovementioned or particularly preferred meaning.

The carbocycles or heterocycles of the above-mentioned guanidinium cations may optionally also be substituted by straight-chain or branched $C_1$- to $C_6$-alkyl, straight-chain or branched $C_1$- to $C_6$-alkenyl, —CN, —$NO_2$, —OH, —F, —Cl, —Br, I, straight-chain or branched $C_1$-$C_6$-alkoxy, —N(R')$_2$, —SR', —S(O)R', —$SO_2$R', —COOH, —C(O)OR', —C(O)R', —C(O)N(R')$_2$, —$SO_2$N(R')$_2$, —C(O)X, —$SO_2$X, —$SO_3$H, substituted or unsubstituted phenyl or unsubstituted or substituted heterocycle, where X and R' have an abovementioned meaning.

Up to four substituents of the thiouronium cation $[C(NR^3R^4)(SR^5)(NR^6R^7)]^+$ or of the uronium cation $[C(NR^3R^4)(OR^5)(NR^6R^7)]^+$ may also be connected in pairs in such a way that mono-, bi- or polycyclic molecules arise.

Without restricting generality, examples of uronium cations or thiouronium cations of this type are indicated below:

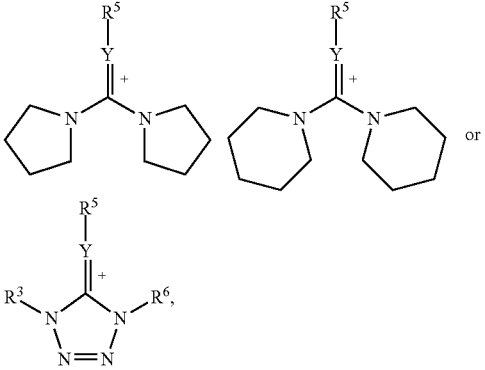

in which Y=S or O
and where the substituents $R^3$, $R^5$ and $R^6$ may have an abovementioned or particularly preferred meaning.

The carbocycles or heterocycles of the above-mentioned guanidinium cations may optionally also be substituted by straight-chain or branched $C_1$- to $C_6$-alkyl, straight-chain or branched $C_1$- to $C_6$-alkenyl, —CN, —$NO_2$, —OH, —F, —Cl, —Br, I, straight-chain or branched $C_1$-$C_6$-alkoxy, —N(R')$_2$, —SR', —S(O)R', —$SO_2$R', —COOH, —C(O)OR', —C(O)R', —C(O)N(R')$_2$, —$SO_2$N(R')$_2$, —C(O)X, —$SO_2$X, —$SO_3$H, substituted or unsubstituted phenyl or unsubstituted or substituted heterocycle, where X and R' have an abovementioned meaning.

The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (5) to (7) may be identical or different here. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

Suitable substituents $R^{1'}$ and $R^{4'}$ of compounds of the formula (8) are in each case, independently of one another, preferably: straight-chain or branched $C_1$- to $C_{20}$, in particular $C_1$- to $C_{12}$-alkyl groups, where one or two carbon atoms which are not adjacent and are not bonded to the heteroatom may be replaced by O, and saturated or unsaturated, i.e. also aromatic, $C_3$- to $C_7$-cycloalkyl groups, which may be substituted by straight-chain or branched $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, pentyl, hexyl, octyl, decyl, methoxymethyl, methoxyethyl, ethoxymethyl, ethoxyethyl, cyclohexyl, phenyl or benzyl. They are very particularly preferably methyl, ethyl, n-butyl or n-hexyl. In pyrrolidine, piperidine, indoline, pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular H, methyl, ethyl, isopropyl, propyl, butyl, sec-butyl, tert-butyl, cyclohexyl, phenyl or benzyl. $R^{2'}$ is particularly preferably H, methyl, ethyl, isopropyl, propyl, butyl or sec-butyl. $R^{2'}$ and $R^{3'}$ are very particularly preferably H.

A straight-chain or branched alkenyl having 2 to 20 C atoms, where a plurality of double bonds may also be present, is, for example, allyl, 2- or 3-butenyl, isobutenyl, sec-butenyl, furthermore 4-pentenyl, isopentenyl, hexenyl, heptenyl, octenyl, —C$_9$H$_{17}$, —C$_{10}$H$_{19}$ to —C$_{20}$H$_{39}$; preferably allyl, 2- or 3-butenyl, isobutenyl, sec-butenyl, preference is furthermore given to 4-pentenyl, isopentenyl or hexenyl. If the compounds are partially fluorinated, at least one H atom is replaced by an F atom. If the compounds are perfluorinated, all H atoms of the corresponding alkyl group have been replaced by F atoms.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —C$_9$H$_{15}$, —C$_{10}$H$_{17}$ to —C$_{20}$H$_{37}$, preferably ethynyl, 1- or 2-propynyl, 2- or 3-butynyl, 4-pentynyl, 3-pentynyl or hexynyl. If the compounds are partially fluorinated, at least one H atom is replaced by an F atom. If the compounds are perfluorinated, all H atoms of the corresponding alkyl group have been replaced by F atoms.

Aryl-C$_1$-C$_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —N(R')$_2$, —CN, —C(O)OH, —C(O)N(R')$_2$, —SO$_2$N(R')$_2$, —C(O)X, —C(O)OR', —C(O)R', —SO$_2$OH, —SO$_2$X, SR', —S(O)R', —SO$_2$R' or NO$_2$, where R' and X have an above-mentioned meaning Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclohexenyl, phenyl, cycloheptenyl, each of which may be substituted by straight-chain or branched C$_1$- to C$_6$-alkyl groups, where the cycloalkyl group or the cycloalkyl group which is substituted by straight-chain or branched C$_1$- to C$_6$-alkyl groups may in turn also be substituted by halogen atoms, such as F, Cl, Br or I, in particular F or Cl, or by —OH, —OR', —N(R')$_2$, —CN, —C(O)OH, —C(O)N(R')$_2$, —SO$_2$N(R')$_2$, —C(O)X, —C(O)OR', —C(O)R', —SO$_2$OH, —SO$_2$X, SR', —S(O)R', —SO$_2$R' or NO$_2$, where R' and X have an above-mentioned meaning.

In the substituents R, R$^2$ to R$^{13}$ or R$^{1'}$ to R$^{4'}$, one or two carbon atoms which are not adjacent and are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$(R')$_2$$^-$, —P(O)R'O—, —C(O)NR'—, —SO$_2$NR', —OP(O)R'O—, —P(O)(N(R')$_2$)NR'—, —P(R')$_2$=N— or —P(O) R', where R' has an above-mentioned meaning.

Halogen denotes F, Cl, Br or I, preferably F, Cl or Br, particularly preferably F or Cl.

In R' or R$^{1*}$, C$_3$- to C$_7$-cycloalkyl is, for example, cyclopropyl, cyclobutyl, cyclopentyl, cyclohexyl or cycloheptyl.

In R' or R$^{1*}$, substituted phenyl denotes phenyl which is substituted by straight-chain or branched C$_1$- to C$_6$-alkyl, straight-chain or branched C$_1$- to C$_6$-alkenyl, CN, N(R")$_2$, —NO$_2$, F, Cl, Br, I, —OH, straight-chain or branched C$_1$-C$_6$-alkoxy, —COOH, —C(O)OR", —C(O)R", —SO$_2$X', —SR", —S(O)R", —SO$_2$R", SO$_2$N(R")$_2$ or SO$_3$H, where R* denotes an unfluorinated, partially fluorinated or perfluorinated straight-chain or branched C$_1$- to C$_6$-alkyl or C$_3$- to C$_7$-cycloalkyl and where X' denotes F, Cl or Br, for example, o-, m- or p-methylphenyl, o-, m- or p-ethylphenyl, o-, m- or p-propylphenyl, o-, m- or p-isopropylphenyl, o-, m- or p-(tert-butyl)phenyl, o-, m- or p-methoxyphenyl, o-, m- or p-ethoxyphenyl, o-, m-, p-(trifluoromethyl)phenyl, o-, m-, p(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In R$^{1'}$ to R$^{4'}$, heteroaryl is taken to mean a saturated or unsaturated mono- or bicyclic heterocyclic radical having 5 to 13 ring members, where 1, 2 or 3 N and/or 1 or 2 S or O atoms may be present and the heterocyclic radical may be mono- or polysubstituted by straight-chain or branched C$_1$- to C$_6$-alkyl, straight-chain or branched C$_1$- to C$_6$-alkenyl, CN, N(R")$_2$, OH, NO$_2$, F, Cl, Br, I, straight-chain or branched C$_1$-C$_6$-alkoxy, —COOH, —C(O)OR", —C(O)R", —SO$_2$X', —SO$_2$N(R")$_2$, —SR", —S(O)R", —SO$_2$R" or SO$_3$H, where R" and X have an above-mentioned meaning.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-C$_1$-C$_6$-alkyl is now taken to mean, analogously to aryl-C$_1$-C$_6$-alkyl, for example, pyridinylmethyl, pyridinylethyl, pyridinylpropyl, pyridinylbutyl, pyridinylpentyl, pyridinylhexyl, where furthermore the heterocycles described above may be linked to the alkylene chain in this way.

HetN$^+$ is preferably

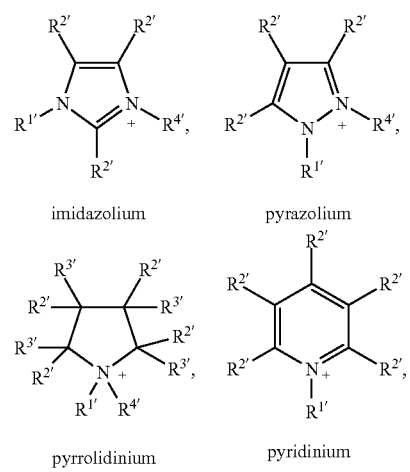

imidazolium     pyrazolium pyrrolidinium     pyridinium

-continued

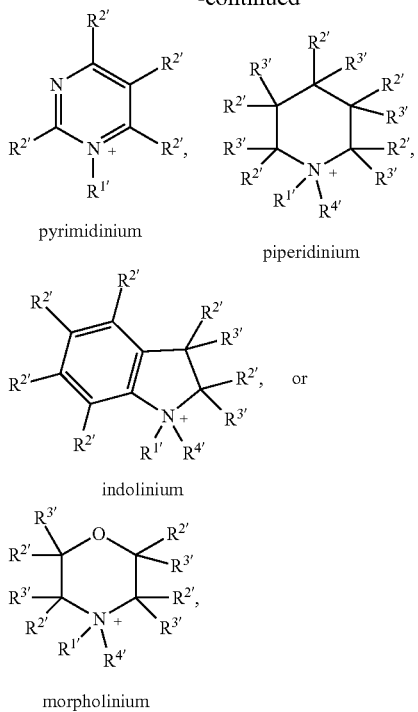

pyrimidinium piperidinium indolinium morpholinium where the substituents $R^{1'}$ to $R^{4'}$ each, independently of one another, have a meaning described above.

The organic cation Kt is particularly preferably selected from the group comprising imidazolium, pyridinium, pyrrolidinium, ammonium or phosphonium cations, as defined above by the formulae indicated and the substituents indicated.

The salt-exchange reaction of the compounds of the formula I with compounds of the formula IV, as described above, is advantageously carried out in water, where temperatures of 0°-100° C., preferably 15°-60° C., are suitable. The reaction is particularly preferably carried out at room temperature (25° C.).

However, the above-mentioned salt-exchange reaction may alternatively also be carried out in organic solvents at temperatures between −30° and 100° C. Suitable solvents here are acetonitrile, dioxane, dichloromethane, dimethoxyethane, dimethyl sulfoxide, tetrahydrofuran, dimethylformamide or alcohol, for example methanol, ethanol or isopropanol.

The following working examples are intended to explain the invention without limiting it. The invention can be carried out correspondingly throughout the range claimed. Possible variants can also be derived starting from the examples. In particular, the features and conditions of the reactions described in the examples can also be applied to other reactions which are not shown in detail, but fall within the scope of protection of the claims.

EXAMPLES

The substances obtained are characterised by means of NMR spectra and X-ray structural analysis. The NMR spectra are measured on solutions in deuterated acetone-$D_6$ or in $CD_3CN$ in a Bruker Avance III spectrometer with deuterium lock. The measurement frequencies of the various nuclei are: $^1H$: 400.17 MHz, $^{11}B$: 128.39 MHz, $^{31}P$: 161.99 MHz and $^{13}C$: 100.61 MHz. The referencing is carried out with an external reference: TMS for $^1H$ and $^{13}C$ spectra and $BF_3 \cdot Et_2O$— for $^{11}B$ spectra.

Example 1

Sodium Dicyanodihydridoborate—$Na[BH_2(CN)_2]$

37.83 g (1.00 mol) of $NaBH_4$ and 302 g (3.04 mol) of trimethylsilyl cyanide, $Me_3SiCN$, are warmed under reflux in inert atmosphere for 2 days (oil-bath temperature is 150° C.). Trimethylsilane, $Me_3SiH$ (b.p. 6.7° C.), formed is collected in a flask in an ice bath. After cooling, the liquid reaction mixture becomes predominantly solid. Excess trimethylsilyl cyanide, $Me_3SiCN$ (101.24 g, 1.02 mol, 98% of the theoretical amount), is removed from the product $Na[BH_2(CN)_2]$ in vacuo. $Na[BH_2(CN)_2]$ is dried in vacuo. The yield is 87.85 g (1.00 mol, 100%).

X-ray structure, $Na[BH_2(CN)_2]$: a=7.8136 (3), b=7.8656 (4), c=16.1764 (7) Å, α=78.489 (4), β=76.882 (3), γ=72.197 (4)°, V=912.75, Z=8, P-1, T=150 K. $^1H\{^{11}B\}$-NMR (solvent: $CD_3CN$; reference: TMS): δ, ppm=0.99 s (2H, $BH_2$).

$^{11}B$-NMR (solvent: $CD_3CN$; reference: $Et_2O.BF_3$): δ, ppm=−42.2 t, $^1J_{B,H}$=95 Hz.

Example 2

Potassium Dicyanodihydridoborate—$K[BH_2(CN)_2]$

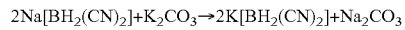

24.8 g (0.282 mol) of sodium dicyanodihydridoborate, $Na[BH_2(CN)_2]$, are dissolved in about 20 ml of water and reacted with 30.2 g (0.219 mol) of $K_2CO_3$. The solution is diluted with 260 ml of tetrahydrofuran and stirred vigorously. The organic phase is separated off, dried using $K_2CO_3$, the tetrahydrofuran is distilled off, and the residue is dried in vacuo. The yield of potassium dicyanodihydridoborate, $K[BH_2(CN)_2]$, is 28.1 g (0.270 mol, 96%) The product is characterised by means of NMR spectra and X-ray analysis.

X-ray structure, $K[BH_2(CN)_2]$: a=7.3073 (3), b=9.5312 (3), c=7.3659 (3) Å, α=90, β=109.965 (5), γ=90°, V=482.18 Z=4, $P2_1/c$, T=150 K.

Example 3

1-Ethyl-3-methylimidazolium dicyanodihydridoborate—EMIM $[BH_2(CN)_2]$

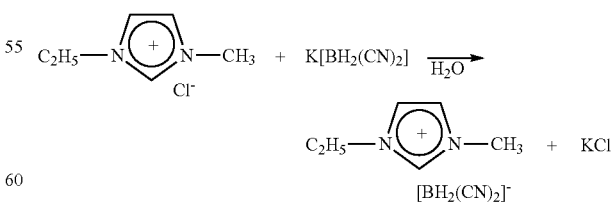

14.04 g (135 mmol) of potassium dicyanodihydridoborate, $K[BH_2(CN)_2]$, and 19.8 g (135 mmol) of 1-ethyl-3-methylimidazolium chloride, [EMIM]Cl, are each dissolved in 20 ml of water and mixed. 1-Ethyl-3-methylimidazolium dicyanodihydridoborate, $[EMIM][BH_2(CN)_2]$, is extracted with 130+50+50 ml of CH₂Cl₂. The combined organic phases are washed with 80 ml of water, dried using Na₂SO₄, and the solvent is distilled off. [EMIM][BH₂(CN)₂] is dried at about 50° C. in vacuo for two days with stirring. The yield is 16.3 g (93 mmol, 69%).

Water content: 44 ppm; chloride content: 18 ppm;
viscosity: 10.2 mPa·s (20° C.).
Decomposition temperature (onset): about 290° C. (DSC/TGA)
$^{11}$B NMR (solvent: CD₃CN; reference: Et₂O.BF₃), δ, ppm: −42.0 t, $^1J_{H,B}$=95 Hz.
$^1$H{$^{11}$B} NMR (solvent: CD₃CN; reference: TMS), δ, ppm: 8.56 br.s (1H, CH); 7.45 d, d (1H, CH), $^3J_{H,H}$=1.8 Hz; 7.39 d, d (1H, CH), $^3J_{H,H}$=1.7 Hz; 4.20 q (2H, CH₂), $^3J_{H,H}$=7.3 Hz; 3.86 s (3H, CH₃); 1.48 t (3H, CH₃), $^3J_{H,H}$=7.3; 0.93 br. s (2H, BH₂).

Example 4

1-Butyl-1-methylpyrrolidinium dicyanodihydridoborate—BMPL [BH₂(CN)₂]

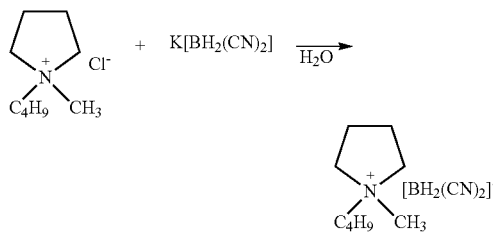

13.9 (134 mmol) g of potassium dicyanodihydridoborate, K[BH₂(CN)₂], and 23.8 g (134 mmol) of 1-butyl-1-methylpyrrolidinium chloride, [BMPL]Cl, are each dissolved in 20 ml of water and mixed. The product, 1-butyl-1-methylpyrrolidinium dicyanodihydridoborate, [BMPL][BH₂(CN)₂], is extracted with 100+100+50 ml of CH₂Cl₂. The combined organic phase are washed with 100 ml of water, dried using Na₂SO₄, and the solvent is distilled off. [BMPL][BH₂(CN)₂] is dried at about 50° C. in vacuo for two days with stirring. The yield of 1-butyl-1-methylpyrrolidinium dicyanodihydridoborate is 23.0 g (111 mmol, 83%).

Chloride content: 21 ppm;
viscosity: 23.6 mPa·s (20° C.).
$^{11}$B NMR (solvent: CD₃CN; reference: Et₂O.BF₃), δ, ppm: −42.0 t, $^1J_{H,B}$=94 Hz.
$^1$H{$^{11}$B} NMR (solvent: CD₃CN; reference: TMS), δ, ppm: 3.45 m (4H, 2CH₂.); 3.27 m (2H, CH₂); 2.99 s (3H, CH₃); 2.19 m (4H, 2CH₂); 1.75 m (2H, CH₂); 1.40 m (2H, CH₂); 0.98 t (3H, CH₃), $^3J_{H,H}$=7.3 Hz; 1.01 s (2H, BH₂).

Example 5

N,N,N-Tributyl-N-methylammonium dicyanodihydridoborate—[(n-C₄H₉)₃CH₃N][BH₂(CN)₂]

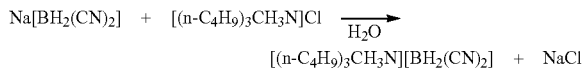

6.68 g (76 mmol) of sodium dicyanodihydridoborate, Na[BH₂(CN)₂], and 17.98 g (76 mmol) of N,N,N-tributyl-N-methylammonium chloride, [(n-C₄H₉)₃CH₃N]Cl, are each dissolved in 20 ml of water and mixed. The product, N,N,N-tributyl-N-methylammonium dicyanodihydridoborate, [(n-C₄H₉)₃CH₃N][BH₂(CN)₂], is extracted with 100+50+50 ml of CH₂Cl₂. The combined organic phases are washed with 100 ml of water, dried using Na₂SO₄, and the solvent is distilled off. [(n-C₄H₉)₃CH₃N][BH₂(CN)₂] is dried at about 50° C. in vacuo for two days with stirring. The yield of tributylmethylammonium dicyanodihydridoborate is 20.0 g (75 mmol, 99%).

Water content: 17 ppm; chloride content: <5 ppm;
viscosity: 158 mPa·s (20° C.).
Decomposition temperature (onset): about 275° C. (DSC/TGA)
$^1$H{$^{11}$B}-NMR (solvent: CD₃CN; reference: TMS): δ, ppm=0.97 t (3CH₃, 9H), $^3J_{H,H}$=7.5 Hz; 1.02 s (2H, BH₂); 1.38 m (3CH₂, 6H); 1.62-1.73 m (3CH₂, 6H); 2.94 s (CH₃, 3H), 3.19 m, (3CH₂, 6H).
$^{11}$B-NMR (solvent: CD₃CN; reference: Et₂O.BF₃): δ, ppm=−41.8 t, $^1J_{B,H}$=94 Hz.

Example 6

Tetrabutylammonium dicyanodihydridoborate—[(n-C₄H₉)₄N][BH₂(CN)₂]

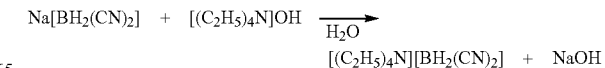

Analogously to Example 5, 5.72 g (65 mmol) of sodium dicyanodihydridoborate, Na[BH₂(CN)₂], are mixed with 45 ml of 40% aqueous tetrabutylammonium hydroxide, [(n-C₄H₉)₄N]OH, and subjected to appropriate work-up. The yield of tetrabutylammonium dicyanodihydridoborate is 19.0 g (62 mmol, 95%).

The product was characterised by means of NMR spectra and X-ray analysis.

Water content: 360 ppm; chloride content: 19 ppm; melting point: 55° C.
Decomposition temperature (onset): about 275° C. (DSC/TGA)
X-ray structure, [(n-C₄H₉)₄N][BH₂(CN)₂]: a=9.4272 (3), b=14.5252 (4), c=15.3664 (5) Å, α=90, β=97.058 (3), γ=90°, V=2088.20, Z=4, P2₁/n, T=110 K.
$^1$H{$^{11}$B}-NMR (solvent: acetone-D₆; reference: TMS): δ, ppm=1.00 t (4CH₃, 12H), $^3J_{H,H}$=7.5 Hz; 1.11 s (2H, BH₂); 1.45 m (4CH₂, 8H); 1.82 m (4CH₂, 8H); 3.42 m, (4CH₂, 8H).
$^{11}$B-NMR (solvent: acetone-D₆; reference: Et₂O.BF₃): δ, ppm=−41.8 t, $^1J_{B,H}$=94 Hz.

Example 7

Tetraethylammonium dicyanodihydridoborate—[(C₂H₅)₄N][BH₂(CN)₂]

Na[BH₂(CN)₂]  +  [(C₂H₅)₄N]OH  →(H₂O)  [(C₂H₅)₄N][BH₂(CN)₂]  +  NaOH

Analogously to Example 5, 9.0 g (103 mmol) of sodium dicyanodihydridoborate, Na[BH$_2$(CN)$_2$], are mixed with 79.5 ml of 20% aqueous tetraethylammonium hydroxide, [(C$_2$H$_5$)$_4$N]OH, and subjected to appropriate work-up. The yield of tetraethylammonium dicyanodihydridoborate is 16.0 g (82 mmol, 80%).

Water content: 192 ppm; chloride content: 30 ppm; melting point: 43° C.

Decomposition temperature (onset): 267° C. (DSC/TGA)

$^1$H{$^{11}$B}-NMR (solvent: acetone-D$_6$; reference: TMS): δ, ppm=1.37 t, t (4CH$_3$, 12H), $^3J_{H,H}$=7.2 Hz, $^3J_{H,N}$=1.9 Hz; 1.07 s (2H, BH$_2$); 3.44 q (4CH$_2$, 8H), $^3J_{H,H}$=7.2 Hz.

$^{11}$B-NMR (solvent: acetone-D$_6$; reference: Et$_2$O.BF$_3$): δ, ppm=−41.7 t, $^1J_{B,H}$=94 Hz.

Example 8

Tetrabutylphosphonium dicyanodihydridoborate—[(n-C$_4$H$_9$)$_4$P][BH$_2$(CN)$_2$]

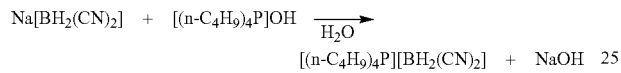

Analogously to Example 5, 5.43 g (62 mmol) of sodium dicyanodihydridoborate, Na[BH$_2$(CN)$_2$], are mixed with 45 ml of 40% aqueous tetrabutylphosphonium hydroxide, [(n-C$_4$H$_9$)$_4$P]OH, and subjected to appropriate work-up. [(n-C$_4$H$_9$)$_4$P][BH$_2$(CN)$_2$] is dried at about 60° C. in vacuo for two days with stirring. The yield of tetrabutylphosphonium dicyanodihydridoborate is 19.0 g (59 mmol, 95%).

Water content: 372 ppm; chloride content: 16 ppm; melting point: 42° C.

Decomposition temperature (onset): 361° C. (DSC/TGA)

$^1$H{$^{11}$B}-NMR (solvent: acetone-D$_6$; reference: TMS): δ, ppm=0.98 t (4CH$_3$, 12H), $^3J_{H,H}$=7.3 Hz; 1.11 br. s (2H, BH$_2$); 1.54 m (4CH$_2$, 8H); 1.65-1.76 m (4CH$_2$, 8H); 2.35-2.45 m, (4CH$_2$, 8H).

$^{11}$B-NMR (solvent: acetone-D$_6$; reference: Et$_2$O.BF$_3$): δ, ppm=−41.7 t, $^1J_{B,H}$=94 Hz.

Example 9

1-Butyl-3-methylpyridinium dicyanodihydridoborate—[BMPy][BH$_2$(CN)$_2$]

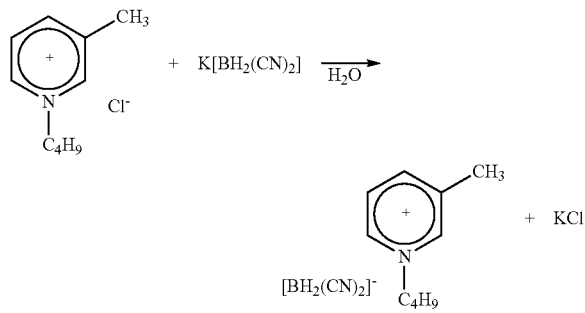

4.09 g (46.6 mmol) of sodium dicyanodihydridoborate, Na[BH$_2$(CN)$_2$], and 8.63 g (46.5 mmol) of 1-butyl-3-methylpyridinium chloride, [BMPy]Cl, are each dissolved in 20 ml of water and mixed. The product, 1-butyl-3-methylpyridinium dicyanodihydridoborate, [BMPy][BH$_2$(CN)$_2$], is extracted with 100+100+50 ml of CH$_2$Cl$_2$. The combined organic phases are washed with 50+50 ml of water, dried using Na$_2$SO$_4$, and the solvent is distilled off. [BMPy][BH$_2$(CN)$_2$] is dried at about 40° C. in vacuo for one day with stirring. The yield of 1-butyl-3-methylpyridinium dicyanodihydridoborate is 9.0 g (41.8 mol, 90%).

$^1$H{$^{11}$B}-NMR (solvent: acetone-D$_6$; reference: TMS): δ, ppm=0.97 t (CH$_3$, 3H), $^3J_{H,H}$=7.5 Hz; 1.02 s (2H, BH$_2$); 1.44 m (CH$_2$, 2H); 2.08 m (CH$_2$, 2H); 2.63 s (CH$_3$, 3H), 4.71 t (CH$_2$, 2H), $^3J_{H,H}$=7.6 Hz; 8.08 d, d (CH, 1H), $^3J_{H,H}$=7.0 Hz; 8.50 d (CH, 1H), $^3J_{H,H}$=8.1 Hz; 8.88 d (CH, 1H), $^3J_{H,H}$=6.1 Hz; 8.95 s (CH, 1H).

$^{11}$B{$^1$H}NMR (solvent: acetone-D$_6$; reference: Et$_2$O.BF$_3$): δ, ppm=−41.7 s

The invention claimed is:

1. Process for the preparation of compounds of the formula I $$Me^+[BH_2(CN)_2]^- \qquad I,$$

where Me$^+$ is a lithium, potassium, sodium, caesium or rubidium cation,
by reaction of a salt of the formula II or of the formula III $$Me^+[BH_4]^- \qquad II,$$

$$Me^+[BH_3(CN)]^- \qquad III,$$

where
Me$^+$ has an above-mentioned meaning, with a trialkylsilyl cyanide, where the alkyl group of the trialkylsilyl cyanide in each case, independently of one another, denotes a linear or branched alkyl group having 1 to 4 C atoms.

2. Process according to claim 1, characterised in that the reaction is carried out at temperatures between 10° C. and 200° C.

3. Process according to claim 1, characterised in that the reaction is carried out without solvent.

4. Process according to claim 1, characterised in that that the trialkylsilyl cyanide is prepared in situ from an alkali-metal cyanide and a trialkylsilyl chloride in the presence of an alkali-metal iodide and optionally iodine.

5. Process according to claim 1, characterised in that the compounds of the formula I is reacted with a compound of the formula IV $$KtA \qquad IV$$

in which
Kt has the meaning of an organic cation or a metal cation, where the cation Kt does not correspond to the cation Me$^+$ employed in the compound of the formula I and the anion A denotes F$^-$, Cl$^-$, Br$^-$, I$^-$, OH$^-$, [HF$_2$]$^-$, [CN]$^-$, [SCN]$^-$, [R$_1$COO]$^-$, [R$_1$OC(O)O]$^-$, [R$_1$SO$_3$]$^-$, [R$_2$COO]$^-$, [R$_2$SO$_3$]$^-$, [R$_1$OSO$_3$]$^-$, [PF$_6$]$^-$, [BF$_4$]$^-$, [HSO$_4$]$^{1-}$, [NO$_3$]$^-$, [(R$_2$)$_2$P(O)O]$^-$, [R$_2$P(O)O$_2$]$^{2-}$, [(R$_1$O)$_2$P(O)O]$^-$, [(R$_1$O)P(O)O$_2$]$^{2-}$, [(R$_1$O)R$_1$P(O)O]$^-$, tosylate, malonate, which may be substituted by straight-chain or branched alkyl groups having 1 to 4 C atoms, [HOCO$_2$]$^-$ or [CO$_3$]$^{2-}$,
where R$_1$ in each case, independently of one another, denotes a straight-chain or branched alkyl group having 1 to 12 C atoms and
R$_2$ in each case, independently of one another, denotes a straight-chain or branched perfluorinated alkyl group having 1 to 12 C atoms and where electroneutrality is taken into account in the formula of the salt KtA.

6. A process according to claim 5, characterised in that Kt denotes an
oxonium cation of the formula $$[(R^o)_3 O]^+ \quad (1)$$

or a sulfonium cation of the formula $$[(R^o)_3 S]^+ \quad (2),$$

where $R^o$ in each case, independently of one another, denotes a straight-chain or branched alkyl group having 1-8 C atoms, unsubstituted phenyl, phenyl which is substituted by $R^{1*}$, OR', N(R')$_2$, CN or halogen or, restricted to sulfonium cations of the formula (2), $(R''')_2 N$, where R' in each case, independently of one another, denotes H, unfluorinated, partially fluorinated or perfluorinated linear or branched $C_1$- to $C_{18}$-alkyl, saturated $C_3$- to $C_7$-cycloalkyl, unsubstituted or substituted phenyl, $R^{1*}$ in each case, independently of one another, denotes unfluorinated, partially fluorinated or perfluorinated linear or branched $C_1$- to $C_{18}$-alkyl, saturated $C_3$- to $C_7$-cycloalkyl, unsubstituted or substituted phenyl and R''' in each case, independently of one another, denotes linear or branched alkyl having 1 to 6 C atoms, or an ammonium cation of the formula (3), $$[NR_4]^+ \quad (3),$$

where

R in each case, independently of one another, denotes H, OR', N(R')$_2$, with the proviso that a maximum of one substituent R in formula (3) is OR' or N(R')$_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, or saturated, partially or fully unsaturated cycloalkyl having 3-7 C atoms, which may be substituted by straight-chain or branched alkyl groups having 1-6 C atoms, where one or two substituents R may be fully substituted by halogens, in particular —F and/or —Cl or where one or more substituents R may be partially substituted by halogens, in particular —F and/or —Cl, and/or by —OH, —OR', —CN, —N(R')$_2$—C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R', and where one or two carbon atoms of the R which are not adjacent and are not in the α-position may be replaced by atoms and/or atom groups selected from the group —O—, —S—, —S(O)—, —SO$_2$—, —SO$_2$O—, —C(O)—, —C(O)O—, —N$^+$(R'$_2$)—, —P(O)R'O—, —C(O)NR'—, —SO$_2$NR'-, —OP(O)R'O—, —P(O)(N(R')$_2$)NR'—, —P(R')$_2$=N— or —P(O)R'—, where R' in each case, independently of one another, denotes H, unfluorinated, partially fluorinated or perfluorinated, linear or branched $C_1$- to $C_{18}$-alkyl, saturated $C_1$- to $C_7$-cycloalkyl, unsubstituted or substituted phenyl and X in each case, independently of one another, denotes halogen, or a phosphonium cation of the formula (4), $$[P(R^2)_4]^+ \quad (4),$$

where $R^2$ in each case, independently of one another, denotes H, OR' or N(R')$_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, or saturated, partially or fully unsaturated cycloalkyl having 3-7 C atoms, which may be substituted by straight-chain or branched alkyl groups having 1-6 C atoms, where one or two substituents $R^2$ may be fully substituted by halogens, in particular —F and/or —Cl or where one or more substituents $R^2$ may be partially substituted by halogens, in particular —F and/or —Cl, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R', and where one or two carbon atoms of the $R^2$ which are not adjacent and are not in the α-position may be replaced by atoms and/or atom groups selected from the group —O—, —S—, —S(O)—, —SO$_2$—, —SO$_2$O—, —C(O)—, —C(O)O—, —N$^+$(R'$_2$)—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' in each case, independently of one another, denotes H, unfluorinated, partially fluorinated or perfluorinated, linear or branched $C_1$- to $C_{18}$-alkyl, saturated $C_3$- to $C_7$-cycloalkyl, unsubstituted or substituted phenyl and X in each case, independently of one another, denotes halogen, or a uronium cation of the formula (5), $$[C(NR^3 R^4)(OR^5)(NR^6 R^7)]^+ \quad (5),$$

or that Kt is a thiouronium cation of the formula (6), $$[C(NR^3 R^4)(SR^5)(NR^6 R^7)]^+ \quad (6),$$

where $R^3$ to $R^7$ each, independently of one another, denote

H, where H is excluded for $R^5$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, or saturated, partially or fully unsaturated cycloalkyl having 3-7 C atoms, which may be substituted by straight-chain or branched alkyl groups having 1-6 C atoms, where one or two of the substituents $R^3$ to $R^7$ may be fully substituted by halogens, in particular —F and/or —Cl, and one or more of the substituents $R^3$ to $R^7$ may be partially substituted by halogens, in particular —F and/or —Cl, and/or —OH, —OR', —N(R')$_2$, —CN, —C(O)OH, —C(O)OR', —C(O)R', —C(O)N(R')$_2$, —SO$_2$NR'$_2$, —C(O)X, —SO$_2$OH, —SO$_2$X, —SR', —S(O)R', —SO$_2$R', —NO$_2$ and where one or two carbon atoms of $R^3$ to $R^7$ which are not adjacent and are not in the α-position may be replaced by atoms and/or atom groups selected from the group —O—, —S—, —S(O)—, —SO$_2$—, —SO$_2$O—, —C(O)—, —C(O)O—, —N$^+$(R'$_2$)—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' in each case, independently of one another, denotes H, unfluorinated, partially fluorinated or perfluorinated, linear or branched $C_1$- to $C_{18}$-alkyl, saturated $C_3$- to $C_7$-cycloalkyl, unsubstituted or substituted phenyl and X in each case, independently of one another, denotes halogen, or a guanidinium cation of the formula (7), $$[C(NR^8 R^9)(NR^{10} R^{11})(NR^{12} R^{13})]^+ \quad (7),$$

where $R^8$ to $R^{13}$ each, independently of one another, denote

H, —CN, N(R')$_2$, —OR', straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, or saturated, partially or fully unsaturated cycloalkyl having 3-7 C atoms, which may be substituted by straight-chain or branched alkyl groups having 1-6 C atoms, where one or two of the substituents $R^8$ to $R^{13}$ may be fully substituted by halogens, in particular —F and/or —Cl, and one or more of the substituents $R^8$ to $R^{13}$ may be partially substituted by halogens, in particular —F and/or —Cl, and/or —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$ and where one or two carbon atoms of $R^8$ to $R^{13}$ which are not adjacent and are not in the α-position may be replaced by atoms and/or atom groups selected from the group —O—, —S—, —S(O)—, —SO$_2$—, —SO$_2$O—, —C(O)—, —C(O)O—, —N$^+$(R'$_2$)—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' in each case, independently of one another, denotes H, unfluorinated, partially fluorinated or perfluorinated, linear or branched C$_1$- to C$_{18}$-alkyl, saturated C$_3$- to C$_7$-cycloalkyl, unsubstituted or substituted phenyl and X in each case, independently of one another, denotes halogen, or a heterocyclic cation of the formula (8), $$[HetN]^{z+} \qquad (8),$$

where

HetN$^{z+}$ denotes a heterocyclic cation selected from the group

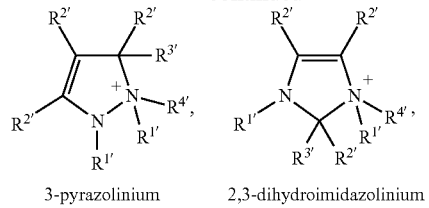

3-pyrazolinium     2,3-dihydroimidazolinium

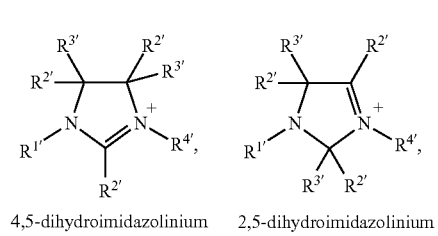

4,5-dihydroimidazolinium     2,5-dihydroimidazolinium

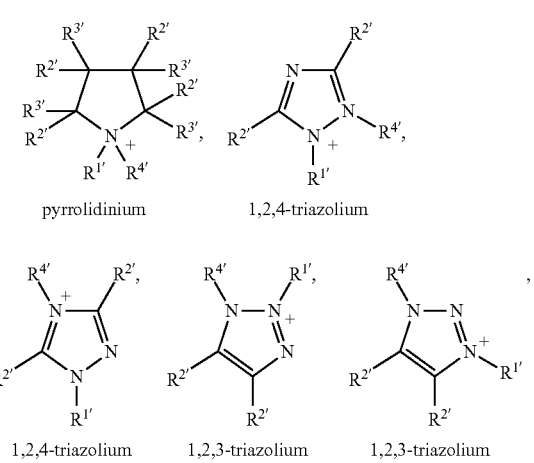

pyrrolidinium     1,2,4-triazolium 1,2,4-triazolium    1,2,3-triazolium    1,2,3-triazolium

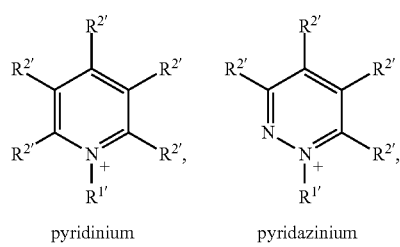

pyridinium     pyridazinium

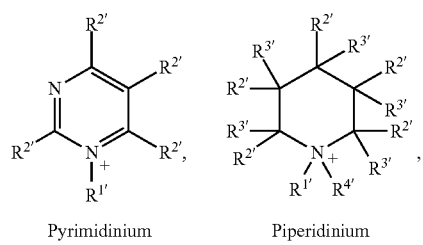

Pyrimidinium     Piperidinium

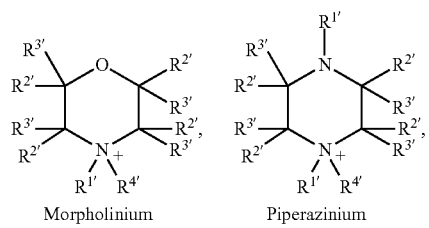

Morpholinium     Piperazinium

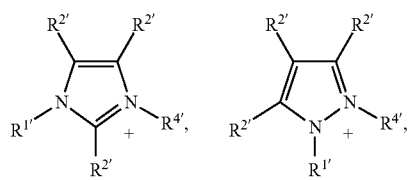

imidazolium     1H-pyrazolium

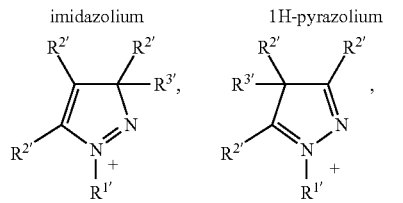

3H-pyrazolium     4H-pyrazolium

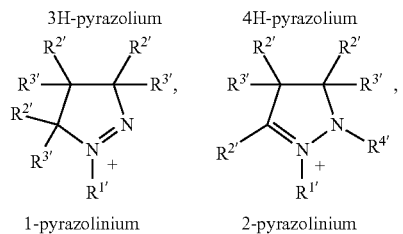

1-pyrazolinium     2-pyrazolinium

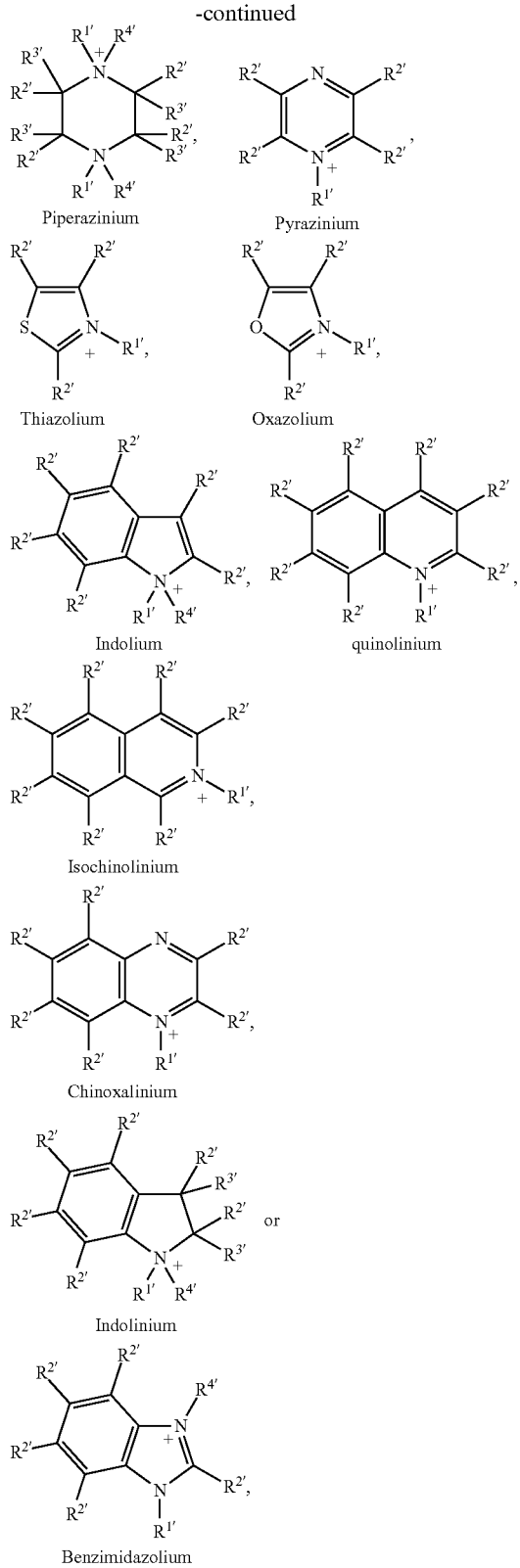

where the substituents

R$^{1'}$ to R$^{4'}$ each, independently of one another, denote H, with the proviso that R$^{1'}$ and R$^{4'}$ are not together H, straight-chain or branched alkyl having 1-20 C atoms, straight-chain or branched alkenyl having 2-20 C atoms and one or more double bonds, straight-chain or branched alkynyl having 2-20 C atoms and one or more triple bonds, or saturated, partially or fully unsaturated cycloalkyl having 3-7 C atoms, which may be substituted by straight-chain or branched alkyl groups having 1-6 C atoms, saturated, partially or fully unsaturated heteroaryl, heteroaryl-C$_1$-C$_6$-alkyl or aryl-C$_1$-C$_6$-alkyl and R$^{2'}$ additionally denotes F, Cl, Br, I, —CN, —OR', —N(R')$_2$, —P(O)R'$_2$, —P(O)(OR')$_2$, —P(O)(N(R')$_2$)$_2$, —C(O)R', —C(O)OR', —C(O)X, —C(O)N(R')$_2$, —SO$_2$N(R')$_2$, —SO$_2$OH, —SO$_2$X, —SR', —S(O)R', —SO$_2$R' and/or NO$_2$, with the proviso that R$^{1'}$, R$^{3'}$ and R$^{4'}$ are then each, independently of one another, H and/or a straight-chain or branched alkyl having 1-20 C atoms and/or a straight-chain or branched alkenyl having 2-20 C atoms and one or more double bonds, where the substituents R$^{1'}$, R$^{2'}$, R$^{3'}$ and/or R$^{4'}$ together may also form a ring system, where one, two or three substituents R$^{1'}$ to R$^{4'}$ may be fully substituted by halogens, in particular —F and/or —Cl, and one or more substituents R$^{1'}$ to R$^{4'}$ may be partially substituted by halogens, in particular —F and/or —Cl, and/or —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$, but where R$^{1'}$ and R$^{4'}$ cannot simultaneously be fully substituted by halogens, and where one or two carbon atoms of the substituents R$^{1'}$ to R$^{4'}$ which are not adjacent and are not bonded to the heteroatom may be replaced by atoms and/or atom groups selected from —O—, —S—, —S(O)—, —SO$_2$—, —SO$_2$O—, —C(O)—, —C(O)O—, —N$^+$(R'$_2$)—, —P(O)R'O—, —C(O)NR'—, —SO$_2$NR'—, —OP(O)R'O—, —P(O)(N(R')$_2$)NR'—, —P(R')$_2$=N— or —P(O)R'—, where R' in each case, independently of one another, denotes H, unfluorinated, partially fluorinated or perfluorinated, linear or branched C$_1$- to C$_{18}$-alkyl, saturated C$_3$- to C$_7$-cycloalkyl, unsubstituted or substituted phenyl and X in each case, independently of one another, denotes halogen, halogen denotes F, Cl, Br or I, or a tritylium cation, or that Kt corresponds to a metal cation from groups 1 to 12 of the Periodic Table, selected from alkali-metal cations, Ag$^+$, Mg$^{2+}$, Cu$^+$, Cu$^{2+}$, Zn$^{2+}$, Ca$^{2+}$, Y$^{+3}$, Yb$^{+3}$, La$^{+3}$, Sc$^{+3}$, Nd$^{+3}$, Tb$^{+3}$, Sm$^{+3}$ or complex (ligand-containing) metal cations which contain rare-earth, transition or noble metals, such as rhodium, ruthenium, iridium, palladium, platinum, osmium, cobalt, nickel, iron, chromium, molybdenum, tungsten, vanadium, titanium, zirconium, hafnium, thorium, uranium or gold.

7. Process according to claim 5, characterised in that the salt-exchange reaction is carried out in an organic solvent or in water.

\* \* \* \* \*

UNITED STATES PATENT AND TRADEMARK OFFICE
CERTIFICATE OF CORRECTION

| | |
|---|---|
| PATENT NO. | : 8,927,714 B2 |
| APPLICATION NO. | : 14/119559 |
| DATED | : January 6, 2015 |
| INVENTOR(S) | : Nikolai Mykola Ignatyev et al. |

It is certified that error appears in the above-identified patent and that said Letters Patent is hereby corrected as shown below:

In the Claims

Column 20, line 19 reads: "1. Process for the preparation of compounds of the formula" should read --1. A process for the preparation of compounds of the formula--.

Column 20, Line 35 reads: "2. Process according to claim 1, characterized in that the" should read --2. A process according to claim 1, wherein the--.

Column 20, Line 38 reads: "3. Process according to claim 1, characterized in that the" should read --3. A process according to claim 1, wherein the--.

Column 20, Line 40 reads: "4. Process according to claim 1, characterized in that that" should read --4. A process according to claim 1, wherein the--.

Column 20, Line 44 reads: "5. Process according to claim 1, characterized in that the" should read --5. A process according to claim 1, wherein a compound--.

Column 20, Line 45 reads: "compounds of the formula I is reacted with a compound of the" should read --wherein a compound of the--.

Column 20, Line 50 reads: "Kt has the meaning of an organic cation or a metal cation," should read --Kt is an organic cation or a metal cation,--.

Column 21, Line 57 reads: "linear or branched $C_1$- to $C_{18}$-alkyl, saturated $C_1$ to" should read --linear or branched $C_1$- to $C_{18}$-alkyl, saturated $C_3$- to--.

Column 26, Line 53 reads: "$Sc^{+3}$, $Nd^{+3}$, $Tb^{+3}$, $Sm^{+3}$ or complex (ligand-containing)" should read --$Sc^{+3}$, $Ce^{+3}$, $Nd^{+3}$, $Tb^{+3}$, $Sm^{+3}$ or complex (ligand-containing)--.

Signed and Sealed this
Fourteenth Day of July, 2015

Michelle K. Lee
*Director of the United States Patent and Trademark Office*

CERTIFICATE OF CORRECTION (continued)
U.S. Pat. No. 8,927,714 B2

Column 27, Line 59 reads: "7. Process according to claim 5, characterized in that the" should read
--7. A process according to claim 5, wherein the--.